US006436136B1

(12) United States Patent
Flodin et al.

(10) Patent No.: US 6,436,136 B1
(45) Date of Patent: Aug. 20, 2002

(54) SHAPED BODIES FOR USE AS IMPLANTS IN HUMAN MEDICINE AND METHOD FOR THE PRODUCTION OF SUCH SHAPED BODIES

(75) Inventors: Per Flodin, Hovås; Katrin Gisselfält, Göteborg, both of (SE)

(73) Assignee: Artimplant AB (SE)

( * ) Notice: Subject to any disclaimer, the term of this patent is extended or adjusted under 35 U.S.C. 154(b) by 0 days.

(21) Appl. No.: 09/530,160

(22) PCT Filed: Oct. 19, 1998

(86) PCT No.: PCT/SE98/01869

§ 371 (c)(1),
(2), (4) Date: Apr. 25, 2000

(87) PCT Pub. No.: WO99/22780

PCT Pub. Date: May 14, 1999

(30) Foreign Application Priority Data

Nov. 3, 1997 (SE) ................................................ 9704003

(51) Int. Cl.$^7$ .................................................. A61F 2/02
(52) U.S. Cl. ....................................... 623/11.11; 623/66
(58) Field of Search ........................... 623/11.11, 16.11, 623/23.58, 23.59, 23.64, 23.71, 66; 528/52, 53, 54, 56; 525/453, 454, 457

(56) References Cited

U.S. PATENT DOCUMENTS

| 5,358,475 | A | * | 10/1994 | Mares et al. ................... 623/66 |
| 5,502,158 | A | * | 3/1996 | Sinclair et al. ............. 528/354 |
| 6,221,997 | B1 | * | 4/2001 | Woodhouse et al. .......... 528/61 |

FOREIGN PATENT DOCUMENTS

| SE | 95/04495 | 6/1997 |
| WO | 89/05830 | 6/1989 |
| WO | 94/09048 | 4/1994 |
| WO | 97/22643 | 6/1997 |

* cited by examiner

Primary Examiner—David J Isabella
(74) Attorney, Agent, or Firm—Lerner, David, Littenberg, Krumholz & Mentlik, LLP

(57) ABSTRACT

Implants are disclosed for use in humans having a rigidity comparable to human bone comprising polyurethane with hydrolysable ester linkages which are spaced apart to provide hydrolysis fragments which are sufficiently small to be resorbed in the human body, the polyurethane comprising a network polymer which is substantially free of urea groups. Methods for the production of such implants are also disclosed.

18 Claims, No Drawings

SHAPED BODIES FOR USE AS IMPLANTS IN HUMAN MEDICINE AND METHOD FOR THE PRODUCTION OF SUCH SHAPED BODIES

TECHNICAL FIELD

The present invention relates to shaped bodies which are to be used as implants in human and veterinary medicine and which primarily consist of pins, screws, discs, ligament fixtures etc. The shaped bodies consist of cured polymer material based on polyurethanes. The invention also comprises a method for the production of the shaped bodies.

PRIOR ART

Both implants and transplants are now commonly used within the medical field. When a human body or an animal is injured as a result of some illness, a damaged organ must often be replaced temporarily or permanently by some kind of implant. The implants may be rigid and be in the form of pins, screws, discs or the like and the material in such implants is usually titanium, steel or the like. The implants may also be soft and, for example, be in the form of pipes which are intended to replace veins or drain out some kind of body fluid and they are then usually made of thermoplastic materials.

Such a soft but resistant implant consists of a polyurethane material and is present in the form of threads or fabric intended to sew together or repair broken ligaments. After the ligaments have been sewn together with this implant, the natural tissue will grow and repair the broken place, whereas the implant slowly disappears and is resorbed by the body fluids. This implant is accordingly temporary and the slow disintegration thereof occurs due to the fact that the polymer chains contain suitable hydrolysable ester groups which are split and which are so closely arranged that the fractions after the hydrolysation are so small that they can be excreted from and/or be metabolised in the body. Such an implant is described in the Swedish patent 9504495-4.

It is of decisive importance for an implant that it is biocompatible, i.e. that it can be accepted by the tissues of the body and does not injuriously affect them. It must also have such properties that it, for example, can replace or support the functions of the damaged organs. Some implants, such as titanium screws for teeth, are intended to be permanent and shall remain in the patient as long as he or she lives. Other implants, which per se are permanent in nature, are however intended to be removed after a long or short period of time.

The Technical Problem

In connection with such implants as pins, screws, discs etc. which are not intended to remain permanently in the patient, a second operation will accordingly be needed after the first operation when the implant is introduced in the body, namely an operation to remove the implant. After the removal of such an irmplant, a cavity is formed which functions as an indication of fracture until new tissue has been formed. This can take from several months to a couple of years and substantially prolongs the time for complete healing.

The metallic implants such as steel and titanium also have a much higher coefficient of elasticity than, for example, human bone. This leads to a reduction in the normal load on the neighbouring tissues, which results in less good healing and sometimes degeneration of the tissue.

Is has long been a desire to bring about a rigid implant for joining of, for example, bones, which implant does not have to be removed later by re-operation and which has a coefficient of elasticity which is comparable to that of the bone.

The Solution

By means of the present invention, the above problem has been solved, making re-operation unnecessary and shaped bodies with a rigidity like that of human bone for use as implants in human medicine as pins, screws, discs, ligament fixtures consisting of polyurethanes with ester links which are hydrolysable in a human body and which give hydrolysis fragments sufficiently small to be resorbed in the human body is brought about which shaped bodies are characterised in that the polymer is a network polymer which substantially lacks urea groups.

According to the invention the ester links should be located so closely that the hydrolysis fragments obtain a molecular weight of at most 100 Dalton by complete hydrolysis.

The invention also comprises a method for the production of shaped bodies, which method is characterised in that a complete mixture of starting materials for forming network polymers of polyurethane containing hydrolysable ester groups and being substantially free from urea groups is introduced in suitable moulds and heated there to a curing temperature during a sufficient length of time to form the form-resistant shaped bodies. The final curing can later take place in heating furnace.

To make compact shaped bodies according to the invention, it is necessary that water is removed from the reaction mixture, preferably by means of a thin film air evaporator or vacuum.

If, however, porous shaped bodies according to the invention are desired then water or some other kind of cell-forming material may be added in controlled amounts before the curing.

According to the invention the curing in the moulds should be carried out a temperature of 70–15° C. in the absence of a catalyst.

However, if a catalyst is used, the curing in the moulds should be performed at a temperature of 30–100° C. Many substances which catalyse the reaction are known, for example aliphatic and aromatic tertiary amines, organometallic compounds, alkali metal salts of carboxyl acids and phenols, etc. As an example, N-ethylmorpholine, dibutyl tin dilaurate can be mentioned. Besides these, compounds exist which both participate in the reaction and catalyse the reaction, for example triethanolamine.

According to the invention, the mixture of starting materials consist, of linear prepolymers having isocyanate end groups and branched polyols, of isocyanate end-terminated polyol prepolymers and diols and/or polyols, of di-isocyanate and diols and polyols or of polyisocyanate and di- or polyols or mixtures thereof According to the invention, it is suitable that the hydrolysable ester groups originate from di- or polyols which may be monoesters, oligo- or polyesters.

According to the invention the di- or polyols in the polyester part suitably consist of ethylene glycol, diethylene glycol, propylene glycol, 1,4-butane diol, polyethylene glycol, oligo- and polytetramethylene oxide glycol, glycerol, trimethylol propane, pentaerythritol, sorbitol, xylitol, glycerol monoallylether and trimethylol propane monoallyl ether.

According to the invention, the acids in the ester groups consist suitably of adipinic acid, succinic acid, glutaric acid, maleinic acid, fumaric acid, bis-carboxymethylethylene glycol, citric acid, tris-carboxymethyl trimethyl propane, bis-carboxymethyl glycerol.

DETAILED DESCRIPTION OF THE INVENTION

The shaped bodies according to the invention consist, as mentioned above, of polyurethanes having certain properties such as adapted suitable hardness having an elasticity coefficient which corresponds to that part of the body, for example a bone part, which is to be supported or replaced and which can be decomposed hydrolytically, whereupon fragments which are sufficiently small for resorption into the human body are obtained. The materials according to the invention must also be biocompatible.

The most important, but not the only, way to produce urethanes is by reaction between an isocyanate and an alcohol. A diisocyanate and a diol in approximately equivalent amount gives a linear polyurethane, whereas a diisocyanate reacted with a polyol gives a network polymer. Such a product is also obtained with polyisocyanates and diols or polyols. Network polymers according to the present invention comprise primarily diisocyanates and polyols. The latter can consist of mixtures of diols and polyols.

Polyurethanes are characterised by urethane groups, —OCONH—, which are separated partly by that radical, $R_1$, which originate from the diisocyanate and partly that radical, $R_2$, which originate from the diol or the polyol. $R_2$ is the one which allows for the largest selection of structures. Theoretically, the isocyanate may also be varied within very wide limits but practically the number is limited due to the difficulty in synthesising isocyanates. This results in that in practice only commercially available isocyanates are used.

$R_2$ originates from diols or polyols and must contain ester groups to be hydrolysable according to the invention. The number of ester groups must be so large that the fragments obtained after complete hydrolysis have a size which is lower than the set limit of 1000 Dalton. The diols or polyols used may be oligo- or polyesters and may have very varying composition. Also the diol or the polyol component may be mixtures of diols or polyols. Both the diol and the acid component may vary within wide limits and be mixtures of diols and/or acids. Ester groups may also be present in $R_1$.

Examples of usable diols and polyols in the polyester part of $R_2$ may be ethylene glycol, diethylene glycol, propylene glycol, 1,4-butane diol, polyethylene glycol, oligo- and polytetramethylene oxide glycol, glycerol, trimethylol propane, pentaerythritol, sorbitol, xylitol, glycerol monoallyl ether, glycerine mono-glycidyl ether, trimethylol propane monoallyl ether. They should not contain functional groups which can react with isocyanites at the later chain extension.

Usable dibasic or polybasic acids in the ester/polyester part of $R_2$ are for instance adipinic acid, succinic acid, glutaric acid, maleinic acid, fumaric acid, bis-carboxymethylethyelene glycol, citric acid, tris-carboxymethyltrimethylol propane, bis-carboxymethylglycerol.

It is very important that the substances in the starting mixture are completely blendable at least at the temperature at which the network forming occurs. If not, an uneven product will be obtained. The starting mixture can consist of a mixture of a linear prepolymer with a branched polyol, of a mixture of a polyol prepolymer with a diol and/or a polyol, of a mixture of a diisocyanate with a diol and/or polyol or a mixture of a polyisocyanate with a diol or a polyol. It is of course possible to combine one or more of these mixtures.

The production of the shaped bodies is carried out by blending the starting materials and introducing them into a mould and heating them therein. The mould can be formed according to the desired the end product, for example for making a screw or a disc or it can give a blank for further machining by, for example, cutting. A technique for the production of blanks is so-called pultrusion by means of which method a continuous rod is formed.

According to the invention, it is important that, if the aim is to obtain a homogeneous material, all water is removed from the reaction mixture. This may be done by carrying out the mixing in a thin layer evaporator or treating the mixture in such an evaporator after the mixing but before the curing. By letting vacuum act on a thin film, any remaining water will be removed from the mixture which during the reaction may cause bubbles to form.

If a porous material (cellular plastic) is desired, such a material may be made by the addition of a controlled amount of water or some other cell-forming material. The technique for this is well known from cellular plastics technology. In addition to water, low-temperature boiling solvents and diazocompounds, among others, may be used as cell-formers. The techniques for regulating the amount of cells, the size of the cells, the proportion of open or closed cells etc., are well known.

Since the implants shall be present in a human or an animal body during long periods and decomposed there, it is very important that no poisonous or unfavourable substances are released. It is therefore preferable that the forming of the three-dimensional network, i.e. the curing in the moulds, is carried out without the aid of releasable catalysts. The temperature in the moulds should therefore be, according to the invention, about 70–150° C. when isocyanate groups react with hydroxyl groups. It may be lower, for example 30–100° C., in the presence of catalysts built into the network, such as triethanole amine.

The time for curing may vary within wide limits depending on the reactivity of the components, but it varies from a few minutes to more than one day. The time which the mixture needs to be in the moulds may only be so long that the shaped body obtains its final shape and can be taken out, further curing being able to be performed in a heating chamber or the like so that the moulds once again can be filled with starting material.

However, it is possible to use catalysts in the starting material if they fulfil the demand for biocompatibility. Such catalysts may consist of tertiary amines such as N-methyl morpholin. Great care with the catalysts is important since the implant is to be used in living beings. Non-catalyst reactions or reactions where the catalyst is build into the network are therefore preferable. In that case the fragments containing the catalyst remainders must be atoxic after hydrolysis.

As mentioned above, the decomposition of the network polymers occurs primarily by hydrolysis of the ester bonds. Between every cross-link point in the network there are such ester groups so that the hydrolysis fragments will consist of sufficiently low-molecular substances. If oligo- or polyesters are part of the polymer then di- or poly acids and di- or polyols will also be created. Several conceivable such substances can be metabolised and thereby be excreted as carbon dioxide and water. The larger fragments are excreted via urine and/or faeces. It is accordingly important that the molecular weight is so low that the substances can pass the membranes of the body.

EXAMPLES 1. 18.82 g of a prepolymer produced from a dicyclohexylmethane 4,4-diisocyanate ($H_{12}$MDI) and polycaprolactone (molecular weight 530 g/mol) was de-watered in vacuum in a thin film evaporator at 80° C. during 3 hours. Thereafter, 1.37 g 2-ethyl-2-(hydroxymethyl)-1,3-propane diol was added. Admixture and further de-watering were carried out at 80° C. during 30 minutes. The homogeneous mixture was weighed out into cylindrical moulds as batches which were heated to 120° C. during 20 hours. The cylinders obtained had a hardness of 70 Shore D.

2. 8.25 g of a branched polyester polyol of trimethylol propane, adipinic acid and diethylene glycol having a hydroxyl equivalent weight of 229 g/mol was mixed with 3,03 g hexamethylene diisocyanate under vacuum in a thin film evaporator at 90° C. during 30 minutes whereupon a homogeneous mixture was obtained. It was weighed out into cylindrical moulds and heated to 120° C. during 20 hours. The product had a hardness of 40 Shore D.

3. 14.95 g of a prepolymer produced from 4,4'-diphenylmethane diisocyanate (MDI) and polycaprolactone (molecular weight 530 g/mol) was de-watered in vacuum in a thin film evaporator at 80° C. during 3 hours. Thereafter 1.2 g unhydrous glycerol was added. Admixture and firther de-watering was carried out at 80° C. during 10 minutes. The homogeneous mixture was weighed out into cylindrical moulds which were heated to 80° C. during 3 hours. The cylinders obtained had a hardness of 70 Shore D.

4. 15.72 g of a prepolymer produced from dicyclohexylmethane-4,4'-diisocyanate ($H_{12}$MDI) and poly-caprolactone (molecular weight 530 g/mol) was de-watered in vacuum in a thin film evaporator at 90° C. during 3 hours. Thereafter 1.47 g triethanol amine was added and the de-watering was continued for a further 30 minutes at 90° C. The homogeneous mixture was weighed out into cylindrical moulds which were heated at 100° C. during 20 hours. The cylinders obtained had a hardness of 60 Shore D.

The invention is not limited to the above-mentioned embodiment examples but it can be varied in different ways within the scope of the patent claims.

What is claimed is:

1. Implants for use in humans having a rigidity comparable to human bone comprising polyurethane including hydrolysable ester linkages, said ester linkages being spaced apart to provide hydrolysis fragments sufficiently small to be resorbed in the human body, said polyurethane comprising a network polymer which is substantially free of urea groups.

2. The implants of claim 1 wherein said implants comprise a member selected from the group consisting of pins, screws, disks and ligaments.

3. The implants of claim 1 wherein said ester linkages are spaced apart to provide hydrolysis fragments having a molecular weight of up to about 1000 Dalton.

4. A method for the production of an implant for use in a human, said implant having a rigidity comparable to human bone and comprising polyurethane including hydrolysable ester linkages spaced apart to provide hydrolysis fragments sufficiently small to be resorbed in the human body, said polyurethane comprising a network polymer produced from predetermined starting materials, and which is substantially free of urea groups, said method comprising mixing together said starting materials for said network polymer, introducing said mixture of said starting materials into a mold, and heating said mold to a predetermined curing temperature for a predetermined period of time to provide a shaped body of said network polymer.

5. The method of claim 4 including removing water from said mixture of said starting materials to form said implant as a compact body.

6. The method of claim 5 wherein said removing of said water from said mixture of said starting materials comprises applying a thin film evaporator and a vacuum.

7. The method of claim 4 including adding a cell-forming material to said mixture of said starting materials to form said implant as a porous body.

8. The method of claim 7 wherein said cell-forming material comprises water.

9. The method of claim 4 wherein said predetermined curing temperature comprises a temperature of from about 70 to 150° C.

10. The method of claim 9 wherein said heating of said mold to said predetermined curing temperature is carried out in the absence of a catalyst.

11. The method of claim 4 wherein said predetermined curing temperature comprises a temperature of from about 30 to 100° C.

12. The method of claim 11 wherein said heating of said mold to said predetermined curing temperature is carried out in the presence of a catalyst.

13. The method of claim 12 wherein said catalyst comprises a tertiary amine.

14. The method of claim 13 wherein said tertiary amine comprises N-methylmorpholin.

15. The method of claim 4 wherein said starting materials are selected from the group consisting of linear prepolymers including isocyanate end groups and branched polyols, isocyanate terminated prepolymers and diols or polyols, and diiosocyanates or polyisocyanates and diols or polyols.

16. The method of claim 15 wherein said diols or polyols comprise monoesters, oligoesters or polyesters, whereby said hydrolysable ester linkages originate therefrom.

17. The method of claim 15 wherein said diols or polyols are selected from the group consisting of ethylene glycol, diethylene glycol, propylene glycol, 1,4-butanediol, polyethylene glycol, oligotetramethylene oxide glycol, polytetramethylene oxide glycol, glycerol, trimethylol propane, pentaerythritol, sorbitol, xylitol, glycerol, monoallylether and trimethylol propane monoallylether.

18. The method of claim 15 wherein said ester groups include an acid selected from the group consisting of adipinic acid, succinic acid, glutaric acid, maleinic acid, fumaric acid, bis-carboxymethylethylene glycol, citric acid, tris-carboxymethyltrimethyl propane and bis-carboxymethyl glycerol.

* * * * *